United States Patent [19]

Berger

[11] Patent Number: 4,550,717

[45] Date of Patent: Nov. 5, 1985

[54] THROAT EXAMINATION DEVICE

[76] Inventor: Karl Berger, 2357 Woodcrest Dr., Johnstown, Pa. 15905

[21] Appl. No.: 598,064

[22] Filed: Apr. 9, 1984

[51] Int. Cl.$^4$ .............................................. A61B 1/06
[52] U.S. Cl. ....................................................... 128/16
[58] Field of Search ............................ 128/16, 15, 11

[56] References Cited

U.S. PATENT DOCUMENTS

| 2,482,116 | 9/1949 | Lanahan | 128/15 |
|---|---|---|---|
| 2,648,329 | 8/1953 | Morch | 128/11 |
| 3,426,749 | 2/1969 | Jefhcott | 128/11 |
| 3,595,222 | 7/1971 | Vellacott | 128/11 |
| 3,598,113 | 8/1971 | Moore | 128/11 |
| 3,614,415 | 10/1971 | Edelman | 128/11 X |
| 3,916,881 | 11/1975 | Heine | 128/16 |
| 3,986,854 | 10/1976 | Scrivo et al. | 128/11 X |
| 4,306,547 | 12/1981 | Lowell | 128/16 X |
| 4,320,745 | 3/1982 | Bhitiyakul et al. | 128/16 X |
| 4,337,761 | 7/1982 | Upsher | 128/16 X |

FOREIGN PATENT DOCUMENTS

| 847948 | 8/1952 | Fed. Rep. of Germany | 128/16 |
|---|---|---|---|
| 858235 | 5/1940 | France | 128/16 |
| 7450 | of 1911 | United Kingdom | 128/15 |

Primary Examiner—William H. Grieb
Attorney, Agent, or Firm—Fidelman, Wolffe & Waldron

[57] ABSTRACT

An optical device is provided for examining the peritonsillar tissue and the area of the throat above the glottis without gagging an alert patient and without the need for the patient to be sedated or semi-comatose. The portion of the device which is inserted into the patient's mouth is cushioned to protect teeth and gums and is covered to provide sterility.

13 Claims, 9 Drawing Figures

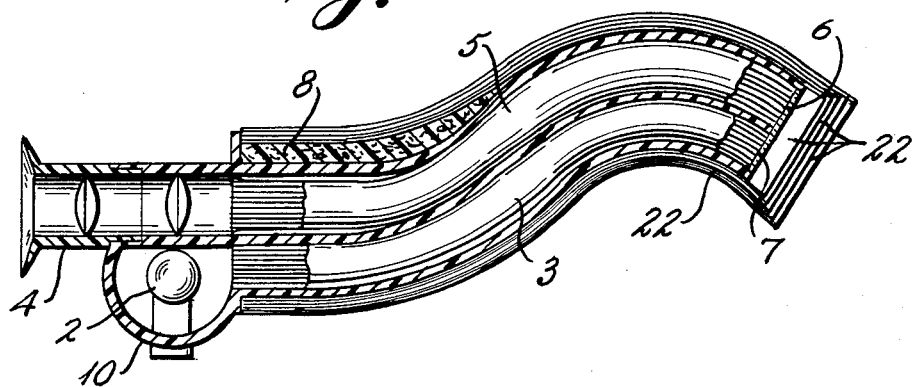
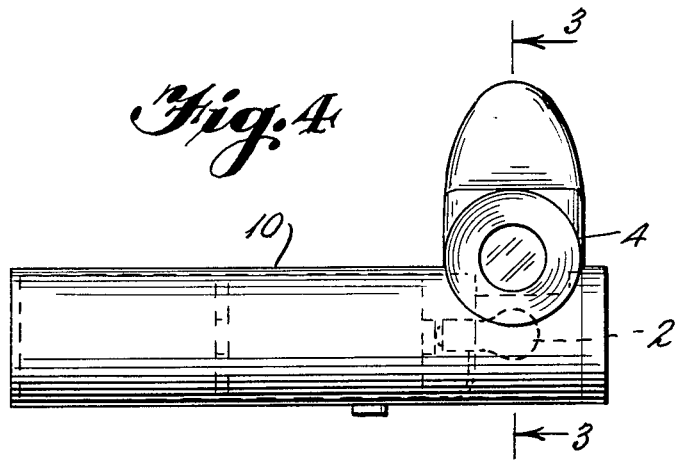
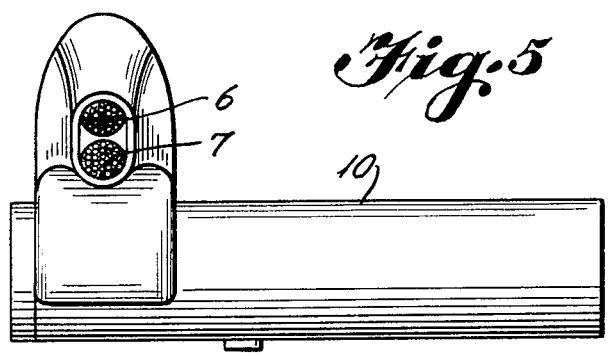

THROAT EXAMINATION DEVICE

CROSS-REFERENCES TO THE PRIOR ART

U.S. Pat. No. 2,648,329—Morch, Laryngoscope, Issued Aug. 11, 1953.
U.S. Pat. No. 3,595,222—Vellacott, et al., Laryngoscope, Issued July 27, 1971.
U.S. Pat. No. 3,598,113—Moore, et al., Disposable Laryngoscope Construction, Issued Aug. 10, 1971.
U.S. Pat. No. 3,614,415—Edelman, Fiber Illuminator, Issued Oct. 19, 1971.
U.S. Pat. No. 4,306,547—Lowell, Rigid Fiberoptic Laryngoscope, Issued Dec. 22, 1981.
U.S. Pat. No. 4,320,745—Bhitiyakul, et al., Fiber Optics Laryngoscope, Issued Mar. 23, 1982.
U.S. Pat. No. 4,337,761—Upsher, Laryngoscope, Issued July 6, 1982.

BACKGROUND AND SUMMARY OF THE INVENTION

The invention is directed to a device for use by a physician in examining the throat of an alert patient without causing gagging and the discomfort and unpleasantness commonly associated therewith.

In the usual throat examination, the patient is told to open his mouth and stick out his tongue while saying AAAAH in order for a light from an observation instrument outside of the patient's mouth to reach the back of the throat, i.e., the tonsils. As may be appreciated, the tongue of a patient is a major obstruction to inspection or examination of this area of the throat, it is often necessary to use a tongue depressor or the like in order to provide a clear line of sight to this area. Such practice can cause gagging resulting in discomfort to an alert patient and difficulty for the examining physician. Prior to the present invention and especially when examining the throats of pediatric patients, it was often necessary to cause gagging in order to achieve the clear line of sight.

The above cross-referenced patents, although not particularly adapted to the same type of examination as the instant invention, are illustrative of devices directed to illumination and visual examination of the larynx. The larynx is much deeper than that area of the throat which the present invention is used to examine, with such prior art devices usually inserted so deeply in the throat as to extend into the larynx. Accordingly, use of laryngoscopes requires that the patient be sedated or at least semi-comatose. Still further, the prior art devices noted above are not adaptable to use in the manner of the instant invention due to their structural configurations. Although the devices of U.S. Pat. Nos. 4,320,745 and 4,306,547, when inverted from their normal use positions, might appear usable in the manner of the instant invention, the light emitting and image receiving end of the device within the patient's mouth would point to the roof of the mouth without illuminating or providing observation of the particular areas with which the instant invention deals.

Hence, it is an object of the present invention to provide a throat examination device by which particular portions of the throat of an alert patient may be examined without the need for gagging the patient.

It is a further object of the invention to provide a throat examination device by which the area of the throat to be examined is illuminated and the illuminated image thereof is viewable outside the patient's mouth by the examining physician.

It is still another object of the invention to locate any electrically conductive parts of the apparatus outside of the mouth of the patient where they will not be susceptible to corrosion and malfunction from contact with the patient's saliva or the like.

It is a further object of the invention to provide a means for protecting the teeth and tissues of the mouth by cushioning a portion of the device which is inserted into the mouth of the patient.

Still further, it is an object of the invention to provide discardable sanitary covers for that portion of the device which is inserted into the mouth of the patient.

In a preferred embodiment of the invention, the device is generally goosenecked in configuration so that a portion thereof is insertable within the open mouth of the patient while requiring little or no extension of the tongue. This configuration provides that a "patient's end" of the device is oriented adjacent the roof of the mouth and directs light to the area of the glottis and tonsils and receives the corresponding image therefrom. A "physician's end" of the device extends outside of the mouth and is provided with a lens system, a light bulb, and a battery handle by which the bulb is powered and the device is manipulated. Fiberoptic bundles respectively conduct light to the patient's end from the bulb and conduct images of the examined area from the patient's end to the focusing lens. At least a portion of the device is provided with a cushioning material in order that the teeth and tissues of the mouth are not subjected to the injury that can occur during engagement thereof with a solid, foreign object. In order to provide good hygiene, a plurality of nestable sterile covers are provided over the portion of the device which is inserted into a patient's mouth.

BRIEF DESCRIPTION OF THE DRAWINGS

FIG. 3 is a cross-section taken along the length of the device of the instant invention, with one embodiment of the hygienic sleeves, and as viewed generally in the direction of arrows 3—3 of FIG. 4.

FIG. 4 is an elevational view of the physician's end of the device.

FIG. 5 is an elevational view of the patient's end of the device.

DETAILED DESCRIPTION OF THE INVENTION

Figure 1A:
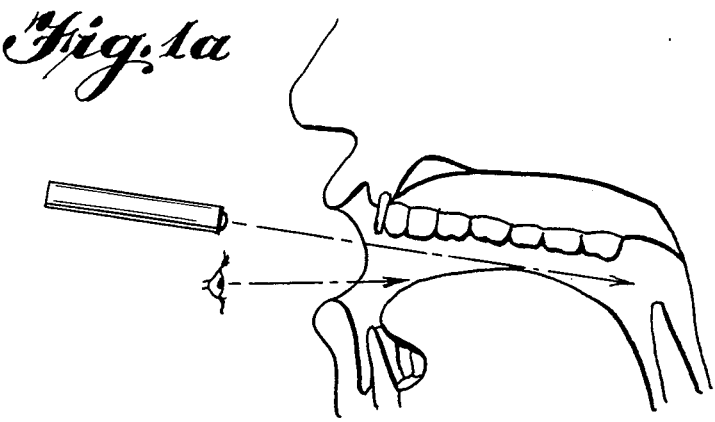
FIGS. 1A and 1B illustrate a prior method and apparatus for examining the tonsils of a patient.
Figure 1B:
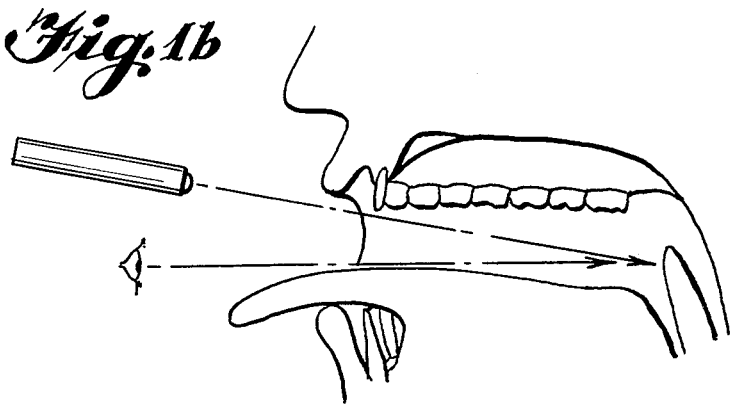

Referring to FIGS. 1A and 1B, it will be apparent that, in order to view that area of the throat including the tonsil, the patient must extend his or her tongue to remove obstruction to the light source and the line of sight of the examining physician. Prior to the instant invention, it was sometimes the case that a tongue depressor or the like would also be required in order to make such an examination, sometimes resulting in gagging of the patient.

Figure 2:
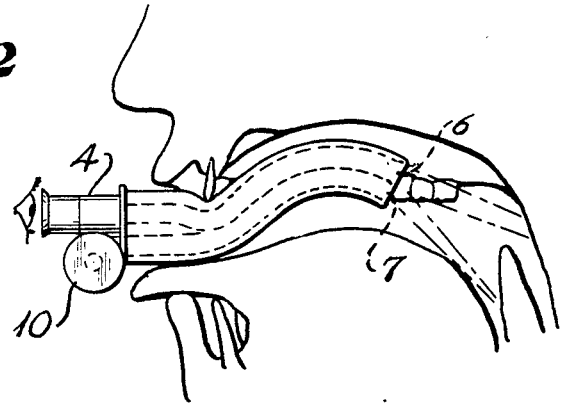
FIG. 2 illustrates use of the device of the instant invention in examining the same area of the throat of a patient as that examined in FIGS. 1A and 1B.

FIG. 2 schematically illustrates the manner with which the device of the instant invention facilitates a throat examination. By use of the device of the instant invention, the distance which the tongue of the patient must be extended from the mouth is reduced or eliminated.

Referring to FIGS. 3-5, the device comprises a generally goosenecked configuration having a fiberoptic bundle 3 for conducting light from a light bulb 2 to a light emitting end 7 and a fiberoptic bundle 5 for conducting an image of the area of the throat being examined from image receiving end 6 to focusing lens system 4. As seen in FIGS. 4 and 5, light bulb 2 is powered by a battery handle 10 such as the standard Welch Allyn battery handle which is removably attachable by a bayonet connection.

In use, one end of the device is inserted into the patient's mouth in the manner illustrated in FIG. 2, thus providing easy illumination and observation of the glottis and peri-tonsillar area of the throat without the usual discomfort and sometimes occurring gagging associated with a tongue depressor or the like. By locating the handle 10 on the side of the device as illustrated in FIGS. 4 and 5, the patient is able to extend the tongue as in FIG. 2 without engaging the handle. In order to protect the upper teeth and the tissue of the roof of the mouth of the patient, the top portion 8 of the device is provided with an appropriate cushioning material.

Figure 6:
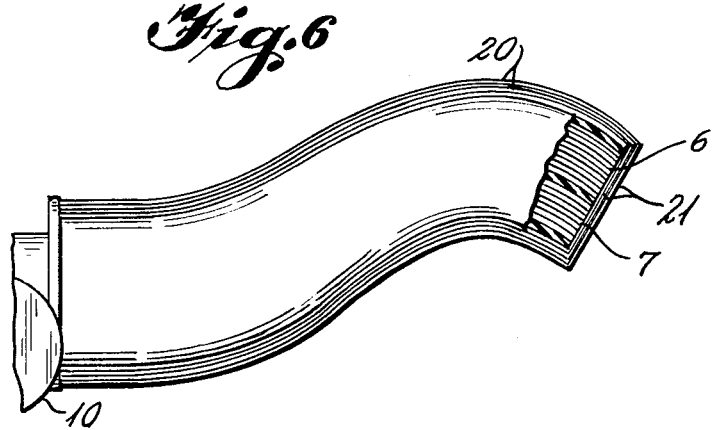
FIG. 6 illustrates another embodiment of nestable, sterile sleeves for covering the patient's end of the device of the instant invention.

Referring to FIG. 6, a plurality of nested sterile sleeves 20 are provided to cover at least that portion of the device extending into the patient's mouth. At the patient end of the device, i.e., the right end of the device as viewed in FIG. 3, the sleeves 20 may differ in structure according to the embodiment being used. As in FIG. 3, the sleeve end 22 may be open and extend past the patient end of the device sufficiently to prevent contact thereof by the tongue. Alternatively and in order to provide even further assurances of sterility, the end of each sleeve 20 in FIG. 6 is closed as in the manner of the tips of the fingers of a rubber glove, provided that the appropriate portion 21 of sleeves 20 are transparent for viewing and at least translucent for lighting the area of the throat being examined. In preparation for examining a patient, the outer sleeve 20 is removed and discarded leaving a next sterile sleeve covering the device to be inserted into the mouth of the patient.

Figure 7:
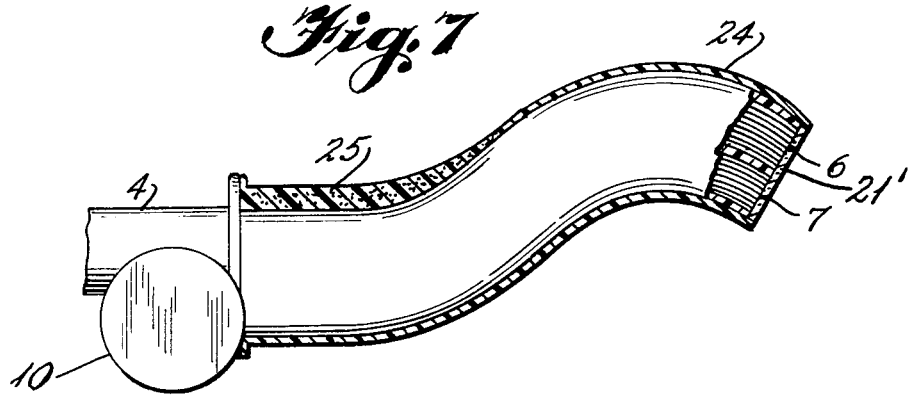
FIG. 7 illustrates still another embodiment of a hygienic sleeve for the throat examination device.
Figure 8:
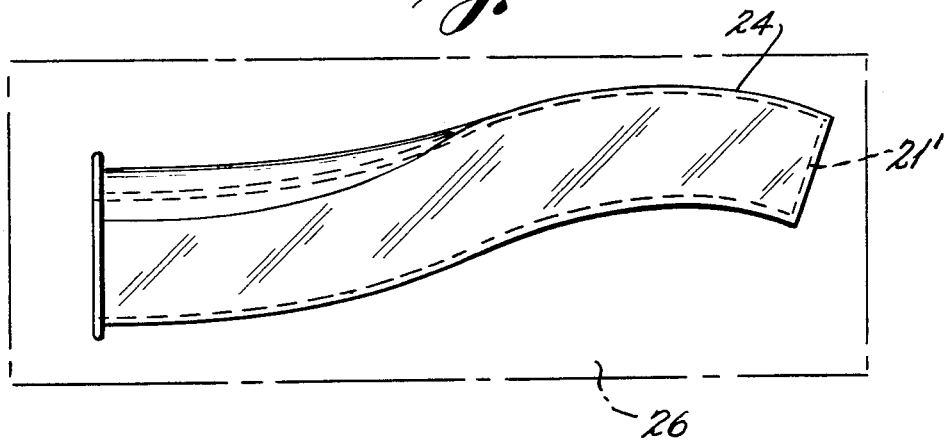
FIG. 8 illustrates a package for the sleeve of FIG. 7.

FIGS. 7 and 8 illustrate still another hygienic cover for the examination device. Cover 24 is sufficiently flexible to slip over the examination device, while being sufficiently stiff to allow ease of handling, and a cushioning material 25 is integrally formed with cover 24. As seen in FIG. 8, a sterile package 26 may enclose each individual cover 24 to provide a one-use, discardable cover. Although not preferred, it is also contemplated that one or more of the covers disclosed may be autoclaveable.

As may be appreciated from the above description, it is neither desirable nor necessary to gag or sedate a patient in order to accomplish examination of the peri-tonsillar tissue and the area above the glottis. Such examination is facilitated by the instant invention by the unique structural configuration and utilization of this device, while providing a sterile device for each use.

It will thus be seen that the objects set forth above, among those made apparent from the preceding description, are effeciently attained and, since certain changes may be made in the construction set forth without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A device for use by a physician in examining the throat of a patient, and comprising:
    a source of light;
    means for directing said light to particular areas of the throat for illumination thereof and having a light emitting end;
    means for directing an image of said particular areas of the throat to a viewing lens, said image direction means having an image receiving end; and
    means for housing said lens, said light directing means, and said image directing means and being configured so that, in use, a portion of said housing is positionable within an alert patient's mouth without causing gagging of the patient, said physician observing said particular areas through said viewing lens which is positioned outside of said mouth and via said image directing means extending into said mouth, said housing portion positioning said light emitting end and said image receiving end above the tongue and adjacent the palate of said patient.

2. A device as in claim 1, and further comprising:
    said housing means being generally goosenecked in configuration in order to effect said positioning.

3. A device as in claim 1, wherein:
    said image directing means and said light directing means comprise respective fiber optic bundles or mirror devices.

4. A device as in claim 1, wherein said light source is located in an outer end of said housing, said housing outer end being positioned outside the patient's mouth during use, and further comprising:
    handle means for manipulating and supporting said device, said handle means being removably attachable to said outer end such that said handle will not interfere with extension of the tongue from the patient's mouth during said examination.

5. A device as in claim 4, said handle comprising:
    a switch for controlling energization of said light source.

6. A device as in claim 5, said handle further comprising:
    at least one battery for energizing said light source according to said controlling switch.

7. A device as in claim 1, and further comprising:
    means for preventing injury to the teeth and tissue of the mouth as by engagement with said housing during use.

8. A device as in claim 7, said injury preventing means comprising:
    a palate portion of said housing, said palate engaging portion having cushioning attached thereto.

9. A device as in claim 1, and further comprising:
    hygiene means for preventing contamination of said device for subsequent examinations.

10. A device as in claim 9, wherein said hygiene means comprises:

a sleeve covering said housing portion which is positionable within the mouth, at least a first portion of said sleeve being transparent and corresponding to said image receiving end, and at least a second portion of said sleeve being at least translucent and corresponding to said light emitting end, such that said image and light are communicated through said sleeve to facilitate said examination while preventing said contamination.

11. A device as in claim 10, said hygiene means further comprising:

a nested plurality of said sleeves being provided such that an outer sleeve is disposable to uncover a sterile next sleeve for use with another patient.

12. A device as in claim 10, said hygiene means further comprising:

said sleeve being resterilizable and removably attachable to said housing in order to effect sterilization of said sleeve.

13. A device as in claim 9, wherein said hygiene means comprises:

plural, nested tubular sleeves substantially covering said housing portion which is positionable within the mouth of said patient, said sleeves extending from said housing portion past said light emitting and image receiving ends sufficiently to avoid contact of said housing by saliva of said patient, each of said sleeves overlapping a next inner sleeve and preventing contamination of an outer surface thereof.

* * * * *